(12) United States Patent
Thum et al.

(10) Patent No.: US 8,216,813 B2
(45) Date of Patent: Jul. 10, 2012

(54) PROCESS FOR ENZYMATICALLY PREPARING CARBOXYLIC ESTERS

(75) Inventors: Oliver Thum, Ratingen (DE); Lutz Hilterhaus, Hamburg (DE); Andreas Liese, Hamburg (DE)

(73) Assignee: Evonik Goldschmidt GmbH, Essen (DE)

( * ) Notice: Subject to any disclaimer, the term of this patent is extended or adjusted under 35 U.S.C. 154(b) by 747 days.

(21) Appl. No.: 12/354,163

(22) Filed: Jan. 15, 2009

(65) Prior Publication Data

US 2009/0181439 A1    Jul. 16, 2009

(30) Foreign Application Priority Data

Jan. 16, 2008    (DE) .................. 10 2008 004 726

(51) Int. Cl.
  *C12P 7/62*        (2006.01)
  *C12P 7/00*        (2006.01)
  *C12P 1/00*        (2006.01)
  *C07C 69/02*       (2006.01)
  *C07C 69/22*       (2006.01)
(52) U.S. Cl. ............... 435/135; 435/41; 435/132; 560/1
(58) Field of Classification Search ................ None
  See application file for complete search history.

(56) References Cited

U.S. PATENT DOCUMENTS

| 4,251,631 | A | 2/1981 | Simon |
| 5,713,965 | A | 2/1998 | Foglia et al. |
| 2006/0074259 | A1 | 4/2006 | Pascaly et al. |
| 2007/0184006 | A1 | 8/2007 | Ferenz et al. |
| 2009/0017519 | A1 | 1/2009 | Thum et al. |
| 2009/0136437 | A1 | 5/2009 | Springer et al. |

FOREIGN PATENT DOCUMENTS

| DE | 25 53 649 | 6/1976 |
| DE | 101 22 551 | 11/2002 |
| EP | 0 413 307 | 2/1991 |
| EP | 0 670 372 | 9/1995 |

OTHER PUBLICATIONS

Katchalski-Katzir, E. and Kraemer, D.M., "EUPERGIT® C, a Carrier for Immobilization of Enzymes of Industrial Potential" Journal of Molecular Catalysis B: Enzymatic 2000, 10, pp. 157-176.*

The Engineering ToolBox "Air Composition", <URL:http://www.engineeringtoolbox.com/air-composition-d_212.html> , online Nov. 21, 2005, 3 pages.*

* cited by examiner

*Primary Examiner* — Chris R Tate
*Assistant Examiner* — Aaron J Kosar
(74) *Attorney, Agent, or Firm* — Frommer Lawrence & Haug LLP

(57) ABSTRACT

Process for enzymatically synthesizing carboxylic esters, characterized in that mixing and discharge of the water of reaction are effected by introducing a gas while achieving low effectiveness ratios EV.

15 Claims, No Drawings

PROCESS FOR ENZYMATICALLY PREPARING CARBOXYLIC ESTERS

This application claims benefit under 35 U.S.C. 119(a) of German patent application 10 2008 004 726.0, filed on 16 Jan. 2008.

Any foregoing applications including German patent application DE 10 2008 004 726.0, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to a novel process for enzymatically preparing carboxylic esters.

STATE OF THE ART

Carboxylic esters are an important group of chemical compounds. Esters of fatty acids are used, for example, frequently as the oil phase in cosmetic formulations. To prepare such compounds proceeding from carboxylic acids, various methods are known. A first overview of this subject is found in: Becker et al., "Organikum", 22nd edition, Wiley-VCH 2004, Weinheim, Germany, page 472 ff.

In recent times, ever more processes based on the use of biocatalysts have found use. The main advantage of these processes typically lies in the mildness of the reaction conditions, which allow a gentle conversion at relatively low temperatures, typically below 100° C. At the same time, a further advantage of the enzymatic processes can frequently also be exhibited, specifically their often high chemo-, regio- or enantioselectivity. The use of heterogeneous biocatalysts, for example enzymes immobilized on inert supports or microorganisms comprising enzymes, has the advantage that they can be removed in simple manner after the reaction and if appropriate be reused. The supports used for the enzyme immobilization are frequently ion exchange resins or polymer beads which possess suitable particle size distributions. Examples of these are the commercial products Novozym 435, Lipozym RM IM or Lipozym TL IM from Novozymes A/S, Bagsvaerd, Denmark, or Amano PS from Amano, Japan. However, many other methods of obtaining immobilized enzyme preparations have also been described, for example in K. Faber, "Biotransformations in Organic Chemistry", Springer: 2000, Berlin, Germany, 384 ff., J. Am. Chem. Soc. 1999, 121, 9487-9496, J. Mol. Catal. B, 2005, 35, 93-99 or in patent application DE 10 2007 031689.7 (EP 2 011 865 A1).

A further condition for ensuring reusability is the minimization of the mechanical forces which act on the catalysts used and cause disintegration of the support and hence a significant particle size reduction, as a result of which the requirement for easy removability is no longer satisfied and large activity losses are often observed. Such forces occur in particular when conventional stirred reactors are used. For example, DE 10 2007 031689.7 (U.S. application Ser. No. 12/168,350) describes the particle size reduction of enzyme immobilizates which occurs after use in stirred flasks.

One means of improving the mechanical stability of the catalysts used lies in the use of a fixed bed reactor. Eur. J. Lipid Sci. Technol. 2003, 105, 601-607 describes, for example, the use of a fixed bed reactor for performing lipase-catalysed esterification. Here, the catalyst is used in the form of a packed bed and the reaction mixture is pumped from a reservoir vessel in circulation through the fixed bed until the desired conversion has been achieved.

The reduction in the reaction temperature, which is desired to obtain maximum product quality, however, also has disadvantages for the industrial implementation of such reactions. The preparation of carboxylic esters from the corresponding acids and alcohols is an equilibrium reaction in which a product, typically the water of reaction formed, has to be removed from the system in order to achieve high conversions. To achieve particularly high conversions, for example of more than 99%, virtually complete removal of the water is necessary. This is typically done by distillation.

It is familiar to the person skilled in the art that the distillative removal of substances from mixtures becomes increasingly difficult with decreasing concentration of the substances to be removed, since the vapour pressure of the substance in mixtures is lowered significantly compared to that in pure form ("Raoult's law"). Therefore, special methods are needed for effective water removal.

A thermodynamically controlled means consists in increasing the temperature of the mixture, for example to significantly above 100° C. However, this method is not an option in enzymatic processes, since the actual advantage of this process, specifically the conduct of the reaction at low temperatures, is first eliminated, and secondly because the enzymes used typically have a significantly shortened service life at such high temperatures.

A further thermodynamically controlled means consists in approximating the ambient pressure very closely to the vapour pressure of the water to be removed in the mixture. The high vacuum required for this purpose is, however, implementable only at a very high level of cost and inconvenience on the production scale, i.e. in plants with several tonnes of capacity.

A further alternative is that of using solvents with which it is either possible to increase the vapour pressure of the water or to distil off the water azeotropically. However, the use of solvents is usually undesired, since they firstly cause additional costs (lower reactor loading, recycling costs, etc.) and, secondly, the absence of solvent residues has to be ensured for many product applications, for example in the cosmetic or pharmaceutical industry, often down to the single-figure ppm range. This is usually possible in principle, but typically requires additional workup steps, for example distillation, extraction or evaporation, which take additional time, and therefore further increase the preparation costs and lower the space-time yields of the processes.

A further variant consists in minimizing the kinetic limitations of the mass transfer from the reaction mixture into the gas space by, for example, increasing the surface area of the mixture, for example in the case of use of falling-film evaporators. Here too, the apparatus complexity is often disproportionately high.

J. Biotech. 2004, 110, 209-217 describes enzymatic ester cleavage for the synthesis of ketoprofen in a sparged reactor. Since the reaction takes place in water, however, it is not water which is removed, which is usually particularly difficult to remove from organic media, but rather 2-chloroethanol. However, only conversions of below 40% were achieved. At these low conversions, as a result of the large excess of water, equilibrium has yet to be attained, and so, for thermodynamic reasons, no product removal at all is necessary, and thus therefore also has no influence on the reaction regime. In addition, the authors find a significant loss of activity after the third use of the enzyme (see FIG. 6 on page 215, loc. cit.), and so the claim for good reusability is not justified. The initially observed higher reaction rate in the sparged reactor in comparison to the fixed bed reactor is explained by the enzyme concentration increased by one third (5 mmol of ester for 50 mg of enzyme in comparison to 40 mmol of ester for 300 mg of enzyme, see footnote to FIG. 6 on page 215, loc. cit.); the increased productivity as a result of termination of the sparged reactions at significantly lower conversions and the associated exploitation of the higher initial rates.

In the industrial performance of esterification reactions, it is usually desirable to minimize the reaction time in order to minimize the preparation costs. Typically, total reaction times should be below 24 hours, preferably below 12 hours, more preferably below 6 hours, especially below 3 hours. For this purpose, it is necessary to obtain an understanding about the rate-determining factors of the reaction to be studied. In the case of the esterification reaction, these may be the amount of catalyst used or, as detailed above, the removal of the water of reaction. In the first case, an increase in the amount of catalyst provides a remedy, in the second case an optimization of the water discharge.

The above-described state of the art typically gives rise to industrial processes for enzymatic esterification in which amounts of enzyme which should theoretically allow a reaction time of below 24 hours, preferably below 12 hours, more preferably below 6 hours, especially below 3 hours, are used, but actually last significantly longer owing to the limitation of the water discharge.

A measure which can be used for the efficiency of the reaction may be the comparison of the actually observed, effective reaction time (ER) to achieve a particular conversion with a calculated, theoretical minimum reaction time (TR). The latter can be calculated to a first approximation from the measured specific activity of the enzyme used in conjunction with the amount used and the Michaelis-Menten constant $K_M$ of this enzyme for the reaction in question. The theoretical background can be found, for example, in: Voet, Voet, "Biochemie" [Biochemistry], 1st edition, Wiley-VCH: 1992, Weinheim, Germany, p. 329-331. To illustrate the efficiency of the process, the quotient of the effective reaction time ER and the theoretical minimum reaction time TR can be formed. This effectiveness ratio (EV) is a very suitable measure which is used hereinafter for the efficiency of enzymatic esterification processes.

The theoretical derivation of the minimum reaction time TR and of the effectiveness ratio EV is described in detail in the "Materials and Methods" section.

In the ideal case, EV is 1; for real reactions to be performed, it is desirable to lower EV as close as possible to 1. Particularly at high conversions, for example greater than 99%, however, the effectiveness ratios observed are significantly greater than 1, often even greater than 5 or greater than 10. Noninventive Examples 1 and 2 show the very high EVs of the prior art processes in conjunction with the appropriate calculation of the EVs in Example 6.

There is therefore still a need for reaction processes for enzymatic preparation of carboxylic esters, which overcome at least one of the disadvantages of the prior art.

OBJECT OF THE INVENTION

It was therefore an object of the present invention to provide a universal process for solvent-free, enzymatic preparation of carboxylic esters, proceeding from carboxylic acids and alcohols, which enables very high conversions coupled with short reaction times and simultaneously a high number of reuses.

Further objects which are not stated explicitly are evident from the context of the description which follows, the examples and the claims.

It has been found that, surprisingly, this object is achieved by a reactor design in which both the mixing of the reactants and the discharge of the water of reaction are achieved through introduction of a gas.

The present invention therefore provides a process for preparing carboxylic acid derivatives, which utilizes this reactor design.

DESCRIPTION OF THE INVENTION

In the process according to the invention, the reaction mixture used, as well as biocatalyst, is mixed by introducing a gas stream and simultaneously freed of water of reaction formed.

Since the process according to the invention can dispense with the use of stirrers in the reaction chamber, and since the mixing is ensured by the gas supply, the mechanical stress, but also the thermal stress induced by the stirrer, on the catalyst particles is reduced to a minimum. These are fundamental prerequisites for reusability of the catalyst.

According to the invention, the gases used may be those which do not enter into any reactions with the reactants, the catalyst or the reactor materials. Preference is given to using air, lean air, oxygen, nitrogen, noble gases or carbon dioxide. The gases used can be applied from suitable pressure vessels, for example gas bottles, or by compressors. The waste air stream can be discharged or reused by suitable measures and circulated.

The catalysts used in accordance with the invention may be those whose mean particle size is such that they can be retained in the reaction vessel without any great pressure drop with the filter systems usually available, i.e. are larger than 0.5 µm, preferably larger than 5 µm, more preferably larger than 10 µm, especially larger than 25 µm.

To produce the enzyme immobilizates, it is possible to use whole cells, resting cells, purified enzymes or cell extracts which comprise the enzymes in question or mixtures thereof. Preference is given to using hydrolytic enzymes, for example lipases, esterases or proteases, for example lipases from *Candida rugosa, Candida antarctica, Pseudomonas* sp., *Thermomyces langosiosus*, porcine pancreas, *Mucor miehei, Alcaligines* sp., cholesterolases from *Candida rugosa*, esterases from the porcine liver, particular preference to using lipases. Accordingly, the enzyme immobilizates preferably comprise enzymes from the class of the hydrolases, preferably lipases.

The supports used to immobilize the enzymes or microorganisms containing enzymes may be inert organic or inorganic supports. The inert supports used are preferably those particulate supports, or those present in the enzyme immobilizate are preferably those, which have a particle size distribution in which at least 90% of the particles have a particle size of 0.5 to 5000 µm, preferably of 10 µm to 2000 µm, more preferably of 25 µm to 2000 µm. The organic supports used may especially be those which comprise or consist of polyacrylate, polymethacrylate, polyvinylstyrene, styrene-divinylbenzene copolymers, polypropylene, polyethylene, polyethylene terepthalate, PTFE and/or other polymers. The support material used may, depending on the enzyme to be immobilized, especially be acidic or basic ion exchange resins, for example Duolite A568, Duolite XAD 761, Duolite XAD 1180, Duolite XAD 7HP, Amberlite IR 120, Amberlite IR 400, Amberlite CG 50, Amberlyst 15 (all products from Rohm and Haas), or Lewatit CNP 105 and Lewatit VP OC 1600 (products from Lanxess, Leverkusen, Germany). The inorganic supports used may be oxidic and/or ceramic supports known from the prior art. More particularly, the inorganic supports used may, for example, be Celite, zeolites, silica, controlled-pore glass (CPG) or other supports, as described, for example, in L. Cao, "Carrier-bound Immobilized Enzymes: Principles, Application and Design", Wiley-VCH: 2005, Weinheim, Germany. More preferably, the inert supports present in the enzyme immobilizate or the inert supports used to prepare the enzyme immobilizates consist of polystyrene, polymethacrylate or polyacrylate.

The present invention therefore provides processes for enzymatically synthesizing carboxylic esters, wherein mixing and discharge of the water of reaction are effected by introducing a gas while achieving low effectiveness ratios EV.

One means of introducing a gas is via sparging, i.e. the bubbling of a chemically inert gas such as air, nitrogen, argon or helium through a liquid. The process of sparging can be used to remove dissolved gases in a liquid or reaction solvent or a liquid byproduct (e.g. water) from a reaction mixture.

The invention further provides a process in which the enzymatic catalyst is fixed covalently or noncovalently in particulate form on a support material.

The invention further provides a process in which the support material has a mean particle size of greater than 0.5 μm.

The invention further provides a process in which the gas used is air, lean air, oxygen, nitrogen, noble gases or carbon dioxide, preferably air or nitrogen.

The invention further provides a process in which the reaction is performed at a temperature of 20° C. to 10° C. The invention further provides a process in which a conversion of 95% is achieved with an effectiveness ratio $EV_{95}$ of <3.0.

The invention further provides a process in which 98% conversion is achieved with an effectiveness ratio $EV_{98}$ of <4.0.

The invention further provides a process in which 99% conversion is achieved with an effectiveness ratio $EV_{99}$ of <5.0.

The invention further provides a process in which 99.6% conversion is achieved with an effectiveness ratio $EV_{99.6}$ of <8.0.

According to the invention, the enzymatic catalyst can be immobilized on the support particles covalently or noncovalently.

Examples of the enzyme immobilizates used in accordance with the invention are Novozym 435, Lipozym RM IM order Lipozym TL IM from Novozymes A/S, Bagsvaerd, Denmark, or Amano PS from Amano, Japan.

The process according to the invention is performed at a temperature of 20° C. to 100° C., preferably of 40° C. to 90° C.

It is found that the process according to the invention, in esterification reactions, can achieve a conversion of 95% with an effectiveness ratio $EV_{95}$ of <3.0, preferably <2.5, more preferably <2.0, especially <1.75.

In addition, it is found that the process according to the invention, in esterification reactions, can achieve a conversion of 98% with an effectiveness ratio $EV_{98}$ of <4.0, preferably <3.00, more preferably <2.50.

In addition, it is found that the process according to the invention, in esterification reactions, can achieve a conversion of 99% with an effectiveness ratio $EV_{99}$ of <5.0, preferably <4.0, more preferably <3.0, especially <2.5.

Finally, it is found that the process according to the invention, in esterification reactions, can achieve a conversion of 99.6% with an effectiveness ratio $EV_{99.6}$ of <8.0, preferably <5.0, more preferably <4.0, especially <3.5.

According to the invention, the process is preferably used to perform reactions of the general formula I

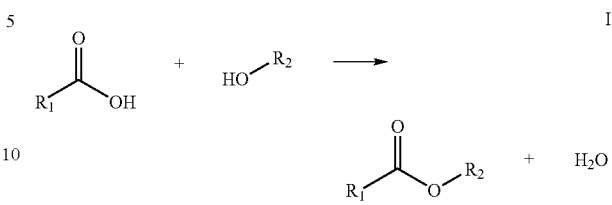

where
$R_1$ is the acyl radical of linear, branched, saturated or unsaturated, optionally additionally substituted carboxylic acids having 2 to 30 carbon atoms,
$R_2$ is a linear, branched, saturated or unsaturated, optionally additionally substituted alkyl radical having from 2 to 30 carbon atoms.

According to the invention, the optional additional substituents of the $R_1$ and $R_2$ radicals may each independently, for example, be hydroxyl groups, ester groups, polyester groups, carbonate groups, polycarbonate groups, ether groups, polyether groups, urethane groups, polyurethane groups, amide groups, polyamide groups, alkylamine groups, dialkylamine groups, halides, siloxane groups, ester groups of inorganic acids, sulphates, phosphates or similar moieties.

In a preferred embodiment, $R_1$ is the acyl radical of commercially available acids, for example acetic acid, propanoic acid, butanoic acid, pentanoic acid, chloroacetic acid, trifluoroacetic acid, ethylhexanoic acid, isononanoic acid, isotridecanoic acid or isostearic acid.

In a further preferred embodiment, the $R_1$ radicals used are acyl radicals of natural fatty acids based on natural vegetable or animal oils. Preference is given to using natural fatty acids, for example caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselic acid, elaidic acid, arachic acid, behenic acid, erucic acid, gadoleic acid, linolenic acid, eicosapentaenoic acid, docosahexaenoic acid or arachidonic acid, alone or in a mixture. The $R_1$ radical may likewise be the acyl radical of polycondensation products of hydroxy-functional acids, for example poly-12-hydroxystearic acid or polyricinoleic acid. The acyl radicals used as the $R_1$ radical may be technical-grade mixtures, for example mixtures of natural fatty acids, for example rapeseed oil fatty acid, soybean oil fatty acid, sunflower oil fatty acid, tallow oil fatty acid, palm oil fatty acid, palm kernel oil fatty acid, coconut fatty acid, which, depending on their specific source and the purification processes used, may be subject to variations in their exact composition, and may also comprise typical secondary constituents, such as unsaturated, functionalized or branched components. In addition, it is also possible to use mixtures of acids of another origin, for example based on petrochemical processes.

In a further preferred embodiment, the $R_2$ radicals used are, for example, the hydrocarbon radicals of propanol, butanol, pentanol, hexanol, octanol or isomers thereof, such as isopropanol, isobutanol, 2-ethylhexanol, isononyl alcohol, isotridecyl alcohol, polyhydric alcohol such as 1,6-hexanediol, 1,2-pentanediol, dihydroxyacetone, 1,2-propylene glycol, 1,3-propylene glycol, neopentyl glycol, trimethylolpropane, pentaerythritol, sorbitol, glycerol, diglycerol, triglycerol, polyglycerol, ethylene glycol, diethylene glycol, triethylene glycol, polyethylene glycol, or amino-functionalized alcohols, such as N,N-dimethylethanolamine. Further examples are the hydrocarbon radicals of alcohols which are prepared by known processes from monobasic fatty acids based on natural vegetable or animal oils having 6 to 30 carbon atoms, especially having 8 to 22 carbon atoms, for example caproic acid, caprylic acid, capric acid, lauric acid, myristic acid, palmitic acid, palmitoleic acid, isostearic acid, stearic acid, 12-hydroxystearic acid, dihydroxystearic acid, oleic acid, linoleic acid, petroselic acid, elaidic acid, arachic acid, behenic acid, erucic acid, gadoleic acid, linolenic acid, eicosapentaenoic acid, docosahexaenoic acid or arachidonic acid, alone or in a mixture.

Examples of the inventive polyether-substituted $R_2$ radicals are the alkyl radicals of polyethylene glycol, polypropylene glycol, polybutylene glycol, polystryrene oxide or copolymers of at least two monomers from the group of ethylene glycol, propylene glycol, butylene glycol, stryrene oxide and polyglycerol. These polyether-substituted radicals may in turn again bear substituents on further OH groups, for example alkyl or alkenyl ethers or alkyl esters.

Examples of the inventive polyester-substituted $R_2$ radicals are polymers which bear free OH groups and are based on ε-caprolactone or γ-valerolactone, for example Placcel L212AL from Daicel.

Examples of the inventive polycarbonate-substituted $R_3$ radicals are polymers which bear free OH groups and are based on dialkyl carbonate and dihydroxyalkyl units, for example Placcel CD220 from Daicel.

Examples of the inventive polysiloxane-substituted $R_2$ radicals are organomodified polysiloxanes bearing free alkyl-OH groups, as obtainable, for example, by hydrosilylating SiH-siloxanes with terminally unsaturated alcohols by methods known to those skilled in the art. In particular, it is possible here to use linear alkenols, such as 5-hexen-1-ol, or allyloxy derivates such as allyloxyethanol, allylglycerol, allylpolyglycerol, allyltrimethylolpropane, allylpolyethylene glycol, allylpolypropylene glycol, or allylpolyethylene glycolpolypropylene glycol copolymers.

The examples of the inventive polysiloxane-substituted $R_1$ radicals are organomodified polysiloxanes bearing free carboxyl groups, as obtainable, for example, by hydrosilylating SiH-siloxanes with terminally unsaturated acids by methods known to those skilled in the art. In particular, it is possible here to use acrylic acid, methacrylic acid or undec-10-enoic acid.

The examples and theoretical considerations which follow are intended to illustrate the present invention in detail, without restricting the scope of protection, which is evident from the description and the claims.

The process according to the invention will be described by way of example hereinafter, without any intention that the invention be restricted to these illustrated embodiments. When ranges, general formulae or compound classes are specified below, they shall encompass not just the corresponding ranges or groups of compounds which are mentioned explicitly, but also all sub-ranges and sub-groups of compounds which can be obtained by selecting individual values (ranges) or compounds. When documents are cited in the context of the present description, their content shall be incorporated fully into the disclosure-content of the present invention. When compounds, for example polymeric support materials, acids or esters, which have different units more than once, are described in the context of the present invention, they may occur in these compounds in random distribution (random oligomer) or in an ordered manner (block oligomer). Information regarding the number of units in such compounds should be interpreted as the mean, averaged over all corresponding compounds.

If the reactants are to be used in the esterification reactions performed in a ratio other than the stoichiometric ratio, the conversion data reported are based on the component used in deficiency.

Materials and Methods:

Novozym 435 (NZ435) is a commercial enzyme immobilizate from Novozymes A/S, Bagsvaerd/Denmark, a lipase B from *C. antarctica* immobilized by adsorption on a polymethacrylate.

Determination of $k_{cat}$ for the Preparation of Myristyl Myristate Catalysed by Novozym 435

10 mg of Novozym 435 were added to 5 ml of equimolar substrate solution (myristic acid and myristyl alcohol) and incubated at 60° C. with stirring. Samples ($V_{sample}$: 50 µl) were taken every 5 min over 25 min and transferred into 950 µl of decane (internal standard: 4 mM dodecane). $k_{cat}$ was determined using the initial product formation rates and was determined to be 7000 µmol*mg$^{-1}$*min$^{-1}$. Myristyl myristate was detected by gas chromatography (Shimadzu 2010, BTX column from SGE; length 25 m, I.D. 0.22 µm; film: 0.25 µm; detector type: FID at 300° C.; injector temperature 275° C. and injection volume 1 µl, split ratio 35.0; carrier gas pressure (helium) 150 kPa; temperature programme: starting temperature 60° C., hold for 1.5 min, temperature rise at 20° C./min, end temperature 250° C., hold for 2.5 min).

Determination of $K_M$ for the Preparation of Myristyl Myristate Catalysed by Novozym 435

10 mg of Novozym 435 were added to 5 ml of equimolar substrate solutions of different concentration (myristic acid and myristyl alcohol, in each case 10 mM to 1000 mM in methylcyclohexane) and incubated at 60° C. with stirring. Samples ($V_{sample}$: 50 µl) were taken every 5 min for each concentration over 25 min and transferred into 950 µl of decane (internal standard: 4 mM dodecane). The plot of the resulting starting rates against the substrate concentration afforded an estimate of a half-maximum reaction rate at $K_M$ of 150 mM. For the sake of simplicity, the constant was not determined for each individual component, but rather for this specific mixture owing to the equimolar consumption in the course of the reaction.

Derivation of the Effectiveness Ratio EV:

The model reaction studied was the preparation of myristyl myristate using immobilized lipase B from *C. antarctica*. It is familiar to the person skilled in the art that the actual reaction rate decreases with falling substrate concentration. The mathematical relationship is described by the Michaelis-Menten equation; see also Voet, Voet, "Biochemie", 1st edition, Wiley-VCH: 1992, Weinheim, Germany, p. 329-331.

This therefore gives rise to equation 1, where [S]=substrate concentration at equilibrium:

$$-\frac{d[S]}{dt} = v = v_{max} \cdot \frac{[S]}{[S] + K_M}, \qquad \text{eq. 1}$$

where $$v_{max} = k_{cat} \cdot c_E, \qquad \text{eq. 2}$$

where $c_E$=enzyme concentration. From this follows equation 3:

$$-\frac{d[S]}{dt} = v = k_{cat} \cdot c_E \cdot \frac{[S]}{[S] + K_M} \qquad \text{eq. 3}$$

To determine the time-dependent conversion, equation 3 can be integrated to provide eq. 4:

$$TR_n = \frac{[S_0] - [S]}{v_{max}} + \frac{K_M}{v_{max}} \cdot \ln\frac{[S_0]}{[S]} \qquad \text{eq. 4}$$

where $TR_n$=theoretical minimum reaction time to achieve the conversion n, $[S_0]$=substrate concentration at t=0 and $[S]$=substrate concentration at conversion n.

For the model reaction, this then gives rise, for example using 0.4 percent by weight of enzyme with $k_{cat}$=7000 µmol*mg$^{-1}$*min$^{-1}$ and $K_M$=150 mmol*L$^{-1}$, for a target conversion of 99.6%, to a $TR_{99.6}$ of 112 minutes.

The comparison of the effective reaction time $ER_n$ of the examples studied with the theoretical reaction time $TR_n$ then provides the effectiveness ratio $EV_n$ for the conversion $C_n$ according to equation 5:

$$EV_n = ER_n/TR_n \qquad \text{eq. 5}$$

EXAMPLES

The invention is further described by the following non-limiting examples which further illustrate the invention, and are not intended, nor should they be interpreted to, limit the scope of the invention.

Example 1

Noninventive

Synthesis of Myristyl Myristate in a Stirred Flask 329 g of myristyl alcohol and 351 g of myristic acid were heated to 60° C. in a 1 L initial charge vessel and mixed by means of a magnetic stirrer. 2.72 g of Novozym 435 were added and the water of reaction formed was removed by applying a vacuum of 5 mbar, and the water was distilled off. The course of the reaction was monitored for ~24 h by means of acid number titration (cf. Table 1).

TABLE 1

| Conversion data for Example 1: | |
|---|---|
| Time [min] | Conversion [%] |
| 0 | 0.0% |
| 60 | 43.9% |
| 122 | 71.1% |
| 180 | 93.0% |
| 355 | 95.1% |
| 640 | 98.0% |
| 802 | 99.0% |
| 1079 | 99.4% |
| 1440 | 99.6% |

Example 2

Noninventive

Synthesis of Myristyl Myristate in a Fixed Bed Reactor—Expensively Modified Falling-Film Process for Removing the Water of Reaction 502 g of myristyl alcohol and 513 g of myristic acid were heated to 60° C. in a 2 1 5-neck flask with bottom outlet and mixed with a mechanical stirrer. 4.06 g of Novozym 435 were charged into a fixed bed heated to 60° C. (height 2 cm, diameter 3 cm). Subsequently, the reaction mixture was pumped with a gear pump through the enzyme-laden fixed bed in circulation via stainless steel tubes heated to 60° C. and back into the flask; the flow rate was set to 50 ml*min$^{-1}$. To remove the water of reaction, a vacuum of 5 mbar was applied and the water was distilled off. To accelerate the removal of water, the reaction mixture, on re-entry into the flask, was allowed to flow down over a distance of about 15 cm in a thin film on the inner wall of a glass column heated to 60° C. The course of the reaction was monitored for ~14 h by means of acid number titration (cf. Table 2).

TABLE 2

| Conversion data for Example 2: | |
|---|---|
| Time [min] | Conversion [%] |
| 0 | 0.0% |
| 180 | 81.1% |
| 240 | 91.0% |
| 300 | 96.2% |
| 420 | 98.2% |
| 540 | 99.1% |
| 840 | 99.6% |

Example 3

Inventive

Synthesis of Myristyl Myristate with Discharge of Water by Sparging 11 010 g of myristyl alcohol and 11 500 g of myristic acid were heated to 60° C. in a glass vessel heated to 60° with an internal diameter of 300 mm and a height of 700 mm. Through a ring sparger mounted at the bottom of the vessel, 5 m$^3$/h of nitrogen were introduced into the mixture. 90 g of Novozym 435 were added and the course of the reaction was monitored for ~6 h by means of acid number titration (cf. Table 3).

TABLE 3

| Conversion data for Example 3: | |
|---|---|
| Time [min] | Conversion [%] |
| 0 | 0.0% |
| 60 | 67.0% |
| 120 | 92.0% |
| 180 | 96.9% |
| 240 | 98.8% |
| 300 | 99.5% |
| 360 | 99.7% |

Example 4

Inventive

Synthesis of Myristyl Myristate with Water Discharge by Sparging 55 305 g of myristyl alcohol and 56 705 g of myristic acid were heated to 60° C. in a glass vessel heated to 60° with an internal diameter of 300 mm and a height of 2500 mm. Through a ring sparger mounted at the bottom of the vessel, 5 m³/h of air were introduced into the mixture. 448 g of Novozym 435 were added and the course of the reaction was monitored for ~9 h by means of acid number titration (cf. Table 4).

TABLE 4

Conversion data for Example 4:

| Time [min] | Conversion [%] |
|---|---|
| 0 | 0.0% |
| 30 | 35.4% |
| 60 | 49.9% |
| 90 | 65.0% |
| 120 | 74.5% |
| 165 | 83.9% |
| 180 | 85.4% |
| 210 | 89.1% |
| 240 | 91.3% |
| 300 | 96.6% |
| 360 | 98.3% |
| 420 | 99.2% |
| 480 | 99.5% |
| 540 | 99.8% |

Example 5

Inventive

Synthesis of Myristyl Myristate with Discharge of Water by Sparging 55 305 g of myristyl alcohol and 56 780 g of myristic acid were heated to 60° C. in a glass vessel heated to 60° with an internal diameter of 300 mm and a height of 2500 mm. Through a ring sparger mounted at the bottom of the vessel, 13.5 m³/h of air were introduced into the mixture. 448 g of Novozym 435 were added and the course of the reaction was monitored for ~7 h by means of acid number titration (cf. Table 5).

TABLE 5

Conversion data for Example 5:

| Time [min] | Conversion [%] |
|---|---|
| 0 | 0.0% |
| 30 | 34.0% |
| 65 | 62.2% |
| 95 | 76.2% |
| 125 | 85.7% |
| 155 | 92.7% |
| 185 | 95.8% |
| 225 | 98.0% |
| 275 | 98.8% |
| 335 | 99.4% |
| 395 | 99.7% |

Example 6

Inventive

Determination of $EV_n$ for Examples 1-5

For Examples 1-5, the time which had been needed to achieve 95%, 98%, 99% and 99.6% conversion was determined (if necessary by interpolation). For these conversions, TR, ER and EV were determined in each case.

TABLE 6

Determination of $TR_n$, $ER_n$ and $EV_n$:

| | Conversion $C_n$ | | | | | | | |
|---|---|---|---|---|---|---|---|---|
| | 95% | | 98% | | 99% | | 99.6% | |
| | $TR_n$ [min]: | | | | | | | |
| | 93 | | 101 | | 106 | | 112 | |
| | ER[min] | $EV_{95}$ | ER[min] | $EV_{98}$ | ER[min] | $EV_{99}$ | ER[min] | $EV_{99.6}$ |
| Example 1* | 350 | 3.75 | 640 | 6.33 | 802 | 7.94 | 1440 | 14.25 |
| Example 2* | 280 | 3.00 | 410 | 4.06 | 530 | 5.24 | 840 | 8.31 |
| Example 3 | 150 | 1.61 | 215 | 2.13 | 250 | 2.47 | 330 | 3.27 |
| Example 4 | 275 | 2.95 | 350 | 3.46 | 400 | 3.96 | 500 | 4.95 |
| Example 5 | 175 | 1.88 | 225 | 2.23 | 295 | 2.92 | 375 | 3.71 |

*Examples 1 and 2 are not inventive.

The analysis shows quite clearly that the esterification under sparging conditions proceeds significantly more rapidly than in conventional stirred flasks or fixed bed reactors under reduced pressure. In addition, it becomes clear that the sparging rate has a significant influence: in Example 5, the sparging rate was increased in comparison to Example 4 from 5 m³/h to 13 m³/h, which lowered EV on average by one third.

Example 7

Re-Use of the Catalyst

Analogously to Examples 3-5, Several Reactions for the synthesis of myristyl myristate were carried out reusing the enzyme catalyst without intermediate purification, and the conversion was determined after 300 minutes (batch sizes in each case 25.6 g of myristic acid, 25.0 g of myristyl alcohol and 0.20 g of Novozym 435, sparging 1500 ml/min of nitrogen. 6 Repetitions were carried out.

TABLE 7

Conversion data for Example 7

| Repetition | Conversion after 300 min |
|---|---|
| 1 | 99.5% |
| 2 | 99.4% |
| 3 | 99.4% |
| 4 | 99.3% |
| 5 | 99.2% |
| 6 | 99.4% |

It becomes clear that, even in the case of repeated use of the catalyst, no significant conversion losses which might be attributable to a deactivation of the catalyst are observed, and that comparable conversions are achieved.

Example 8

Preparation of Decyl Cocoate 429 g of decanol (Aldrich, OHN: 340 $mg_{KOH}/g$) and 553 g of coconut fatty acid (Edenor HK 8-18, from Cognis, AN: 271.4 $mg_{KOH}/g$) were heated to 60° C. in a glass vessel heated to 60° with an internal diameter of 100 mm and a height of 500 mm. Through a glass frit mounted at the bottom of the vessel, 3 l/min of nitrogen were introduced into the mixture. 3.9 g of Novozym 435 were added. After 9 hours, the reaction mixture had attained an acid number of 0.86 $mg_{KOH}/g$.

Example 9

Preparation of a Polyetherester 418.7 g of a polyethylene/polypropylene glycol (molar mass 2790 g/mol, OHN: 40.2 $mg_{KOH}/g$, composition: 52% ethylene glycol, 48% propylene glycol) and 55.3 g of undec-10-enoic acid (2 equivalents, Aldrich, AN: 304.4 $mg_{KOH}/g$) were heated to 60° C. in a glass vessel heated to 60° with an internal diameter of 100 mm and a height of 500 mm. Through a glass frit mounted at the bottom of the vessel, 2 l min of nitrogen were introduced into the mixture. 9.5 g of Novozym 435 were added. After 23 hours, the reaction mixture had attained an acid number of 1.0 $mg_{KOH}/g$.

Example 10

Preparation of a Polyester 404.6 g of diethyl adipate (Aldrich) and 236.4 g of 1,6-hexanediol (Aldrich) were heated to 60° C. in a glass vessel heated to 60° with an internal diameter of 100 mm and a height of 500 mm. Through a glass frit mounted at the bottom of the vessel, 2 l/min of nitrogen were introduced into the mixture. 6.4 g of Novozym 435 were added. After 24 hours, a conversion of 94% based on diethyl adipate was determined by $^1$H NMR. A GPC analysis (Agilent 1100, 1 ml/min of THF, polystyrene as standard) showed the formation of a polymer with $M_W$=3819 g/mol and $M_N$=1854 g/mol.

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A process for enzymatically synthesizing a carboxylic ester, the process comprising:
    mixing an alcohol and a carboxylic acid with an enzyme capable of, and under conditions sufficient for, synthesizing a carboxylic ester, thereby producing a reaction mixture comprising said carboxylic ester and water;
    introducing a gas to the reaction mixture at a flow rate sufficient to discharge the water from the reaction mixture;
    wherein the process provides a lower effectiveness ratio (EV) than a corresponding process in which gas is not introduced to the reaction mixture; and
    wherein the enzyme is covalently or noncovalently fixed in particulate form to a support material.
2. The process according to claim 1, wherein the support material has a mean particle size of greater than 0.5 μm.
3. The process according to claim 2, wherein the introduced gas is selected from the group consisting of air, lean air, oxygen, nitrogen, noble gases, and carbon dioxide.
4. The process according to claim 2, wherein said mixing step comprises mixing at a temperature of 20° C. to 100° C.
5. The process according to claim 2, wherein a 95% conversion of the carboxylic acid to said carboxylic ester is achieved with an effectiveness ratio $EV_{95}$ of <3.0.
6. The process according to claim 2, wherein 98% conversion of the carboxylic acid to said carboxylic ester is achieved with an effectiveness ratio $EV_{98}$ of <4.0.
7. The process according to claim 2, wherein 99% conversion of the carboxylic acid to said carboxylic ester is achieved with an effectiveness ratio $EV_{99}$ of <5.0.
8. The process according to claim 2, wherein 99.6% conversion of the carboxylic acid to said carboxylic ester is achieved with an effectiveness ratio $EV_{99.6}$ of <8.0.
9. The process according to claim 3, wherein the gas is air or nitrogen.
10. The process according to claim 9, wherein said mixing step comprises mixing at a temperature of 20° C. to 100° C.
11. The process according to claim 10, wherein 99.6% conversion of the carboxylic acid to said carboxylic ester is achieved with an effectiveness ratio $EV_{99.6}$ of <8.0.
12. The process according to claim 11, wherein 99.6% conversion of the carboxylic acid to said carboxylic ester is achieved with an effectiveness ratio $EV_{99.6}$ of <5.0.
13. The process according to claim 1, wherein the introducing of the gas is via sparging.
14. The process according to claim 12, wherein the introducing of the gas is via sparging.
15. The process according to claim 12,
    wherein the alcohol is myristyl alcohol;
    wherein the carboxylic acid is myristic acid; and
    wherein the carboxylic ester is myristyl myristate.

* * * * *